(12) United States Patent
Geiger et al.

(10) Patent No.: US 8,377,145 B1
(45) Date of Patent: Feb. 19, 2013

(54) ADJUSTABLE PYLON FOR PROSTHETIC LIMB

(75) Inventors: Richard Geiger, Boalsburg, PA (US); Jeremy Frank, Pine Grove Mills, PA (US); Jeff Quelet, Hagerstown, MD (US); Jeffery M Brandt, Chester Springs, PA (US)

(73) Assignee: Kinetic Revolutions, LLC, Fredrick, MD (US)

( * ) Notice: Subject to any disclaimer, the term of this patent is extended or adjusted under 35 U.S.C. 154(b) by 0 days.

(21) Appl. No.: 13/038,826

(22) Filed: Mar. 2, 2011

(51) Int. Cl.
*A61F 2/80* (2006.01)
(52) U.S. Cl. .......................................................... 623/38
(58) Field of Classification Search .............. 623/27–38; 248/200.1, 354.4
See application file for complete search history.

(56) References Cited

U.S. PATENT DOCUMENTS

| | | | | |
|---|---|---|---|---|
| 5,575,790 | A | * 11/1996 | Chen et al. | 606/60 |
| 2003/0220701 | A1 | * 11/2003 | Steinbarger et al. | 623/38 |
| 2005/0171617 | A1 | * 8/2005 | Curtis | 623/38 |

* cited by examiner

*Primary Examiner* — Bruce E Snow
(74) *Attorney, Agent, or Firm* — John J. Elnitski, Jr.

(57) ABSTRACT

An adjustable pylon to be used with a prosthetic limb. The adjustable pylon including a fixed tube having an attachment end to attach to the prosthetic limb, a receiving end, and a retainer bulkhead with a hole. The adjustable pylon including an adjustable tube having an attachment end to attach to the prosthetic limb, an insert end sized to fit inside the fixed tube, a threaded bulkhead with a threaded hole inside the adjustable tube. The adjustable pylon including a length adjustment screw including a threaded body and a centering post.

11 Claims, 12 Drawing Sheets

ADJUSTABLE PYLON FOR PROSTHETIC LIMB

BACKGROUND

The present invention generally relates to prosthetic limbs. More specifically, the present invention relates to pylons used with prosthetic legs.

Prosthetic legs typically include what is referred to as a pylon between a prosthetic foot and either the calf of the wearer or a prosthetic calf. The pylon is typically a metal or carbon fiber tube that attaches between the calf and the foot. The pylon is cut to size, so that it provides the proper length between the calf and the foot. This process is time consuming and limited in accuracy, because it requires a practitioner to manually cut the shaft to length. An additional problem with using a single tube is that there is no means to adjust the length between the calf and the foot by the practitioner or user is a situation arises that requires a different length. Examples are use of different type of shoe, use of a different prosthetic foot and physical body changes in the user. What is needed is an adjustable pylon, which allows a faster and more accurate length adjustment by a practitioner and could enable the practitioner or user to change the length of the pylon when required.

It is an object of the present invention to provide an adjustable pylon between the calf and the foot to allow adjustment in length of the pylon by a user.

SUMMARY OF THE INVENTION

An adjustable pylon to be used with a prosthetic limb. The adjustable pylon including a fixed tube having an attachment end to attach to the prosthetic limb, a receiving end, and a retainer bulkhead with a hole. The adjustable pylon including an adjustable tube having an attachment end to attach to the prosthetic limb, an insert end sized to fit inside the fixed tube, a threaded bulkhead with a threaded hole inside the adjustable tube. The adjustable pylon including a length adjustment screw including a threaded body and a centering post.

DETAILED DESCRIPTION

Figure 1:
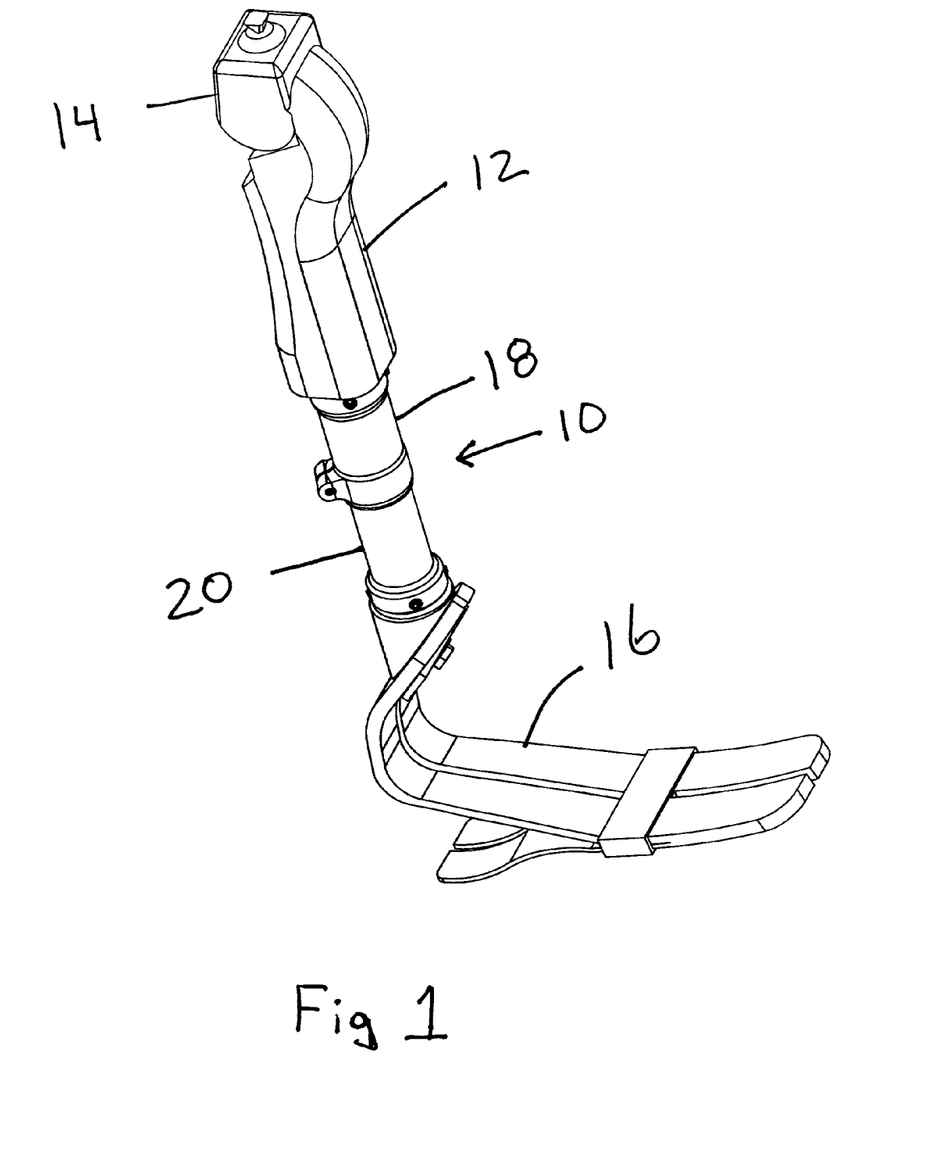
FIG. 1 is a perspective view of an adjustable pylon as part of a prosthetic limb according to the present invention.
Figure 2:
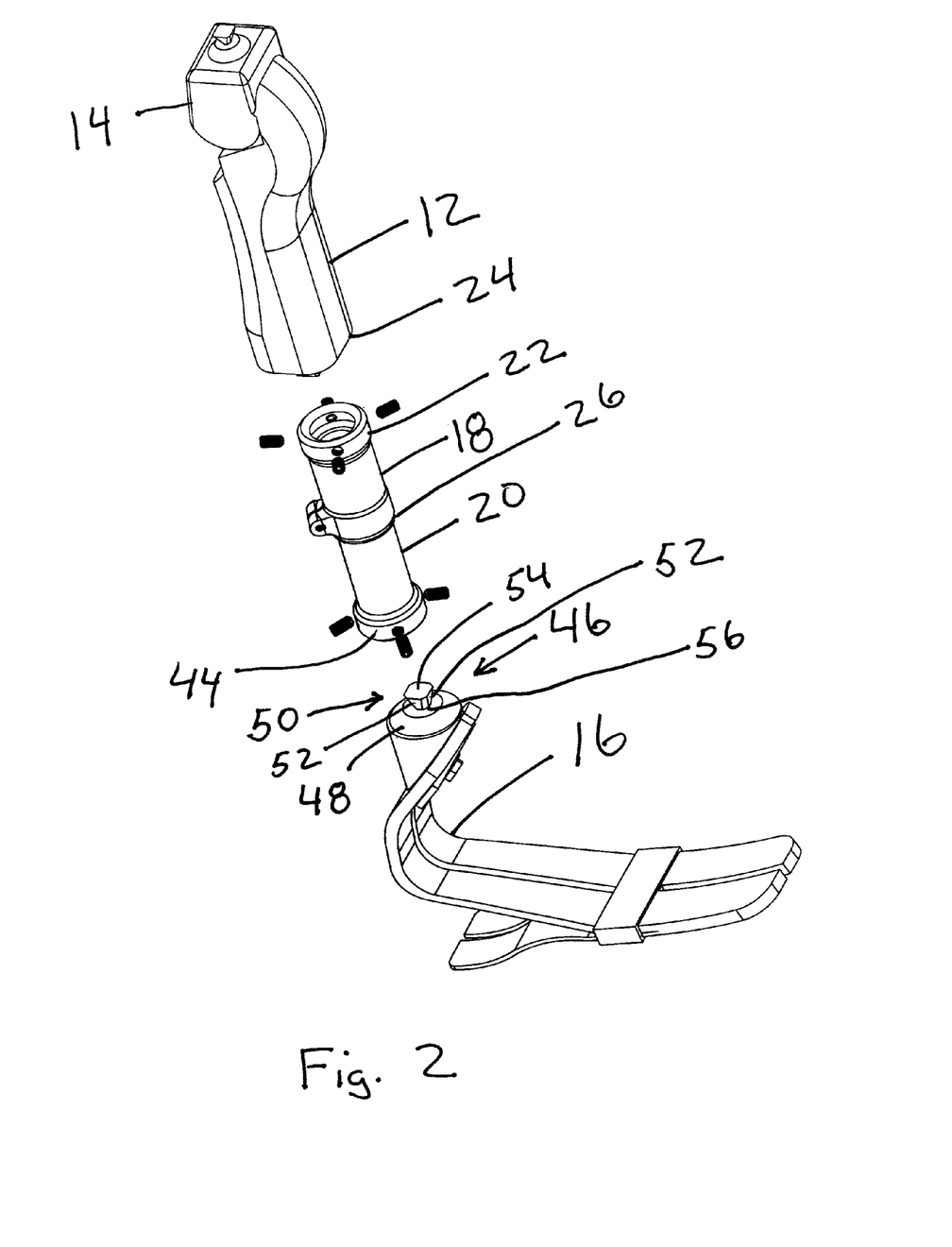
FIG. 2 is a perspective exploded view of an adjustable pylon as part of a prosthetic limb according to the present invention.
Figure 3:
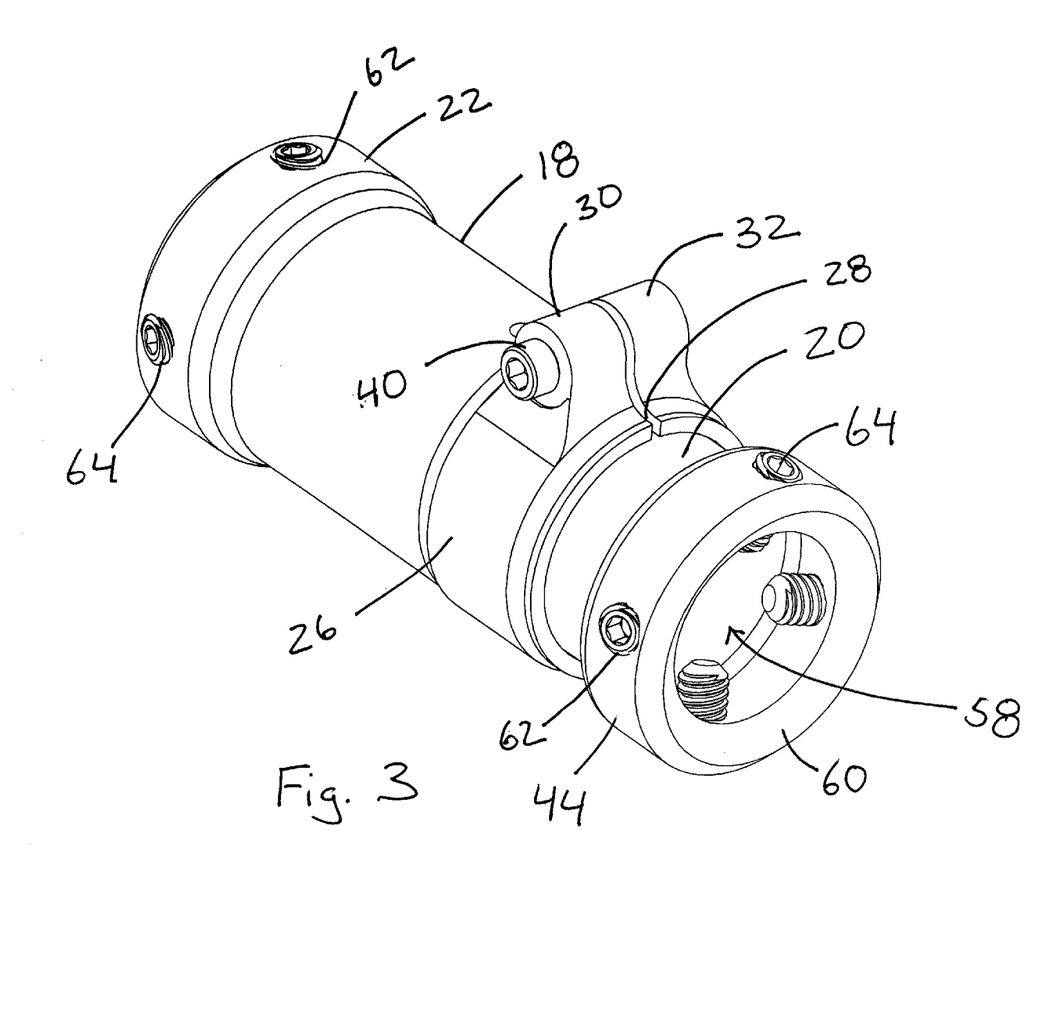
FIG. 3 is a perspective view of an adjustable pylon according to the present invention.
Figure 4:
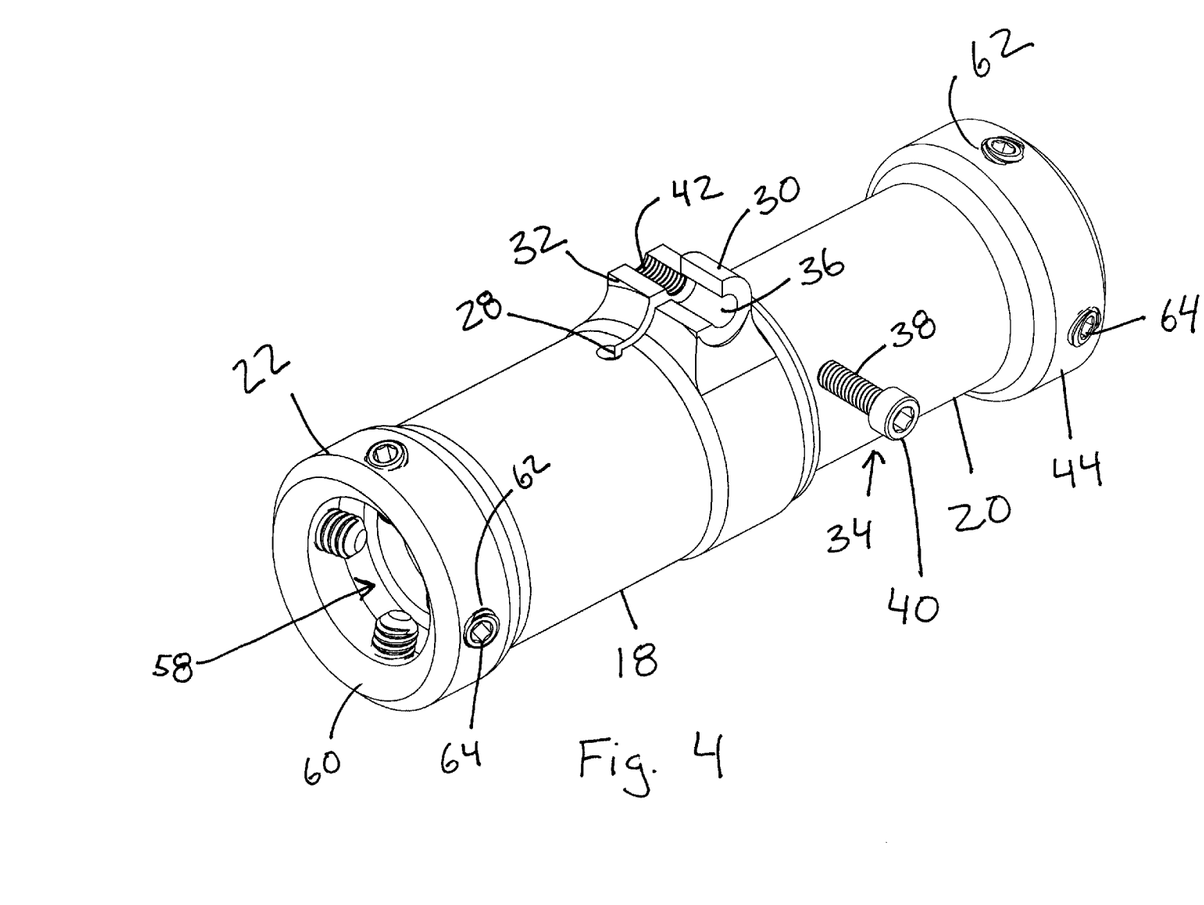
FIG. 4 is a perspective view of an adjustable pylon according to the present invention.

The present invention is an adjustable pylon 10 for a prosthetic limb. The pylon 10 is shown mounted between a prosthetic calf 12 with knee 14 and a prosthetic foot 16, as shown in FIGS. 1-2. The pylon 10 includes a fixed tube 18 and an adjustable tube 20, as shown in FIGS. 1-4. The fixed tube 18 and adjustable tube 20 are shown as a cylinder shape, but could be any shape of tube. The fixed tube 18 includes a fixed tube attachment head 22 at one end that attaches to a bottom 24 of the prosthetic calf 12. The fixed tube 18 includes a receiving end 26 to receive the adjustable tube 20 into the fixed tube 18. The receiving end 26 of the fixed tube 18 includes clamping groove 28. The receiving end 26 of the fixed tube 18 includes a first clamp bulkhead 30 on one side of the clamping groove 28 and a second clamp bulkhead 32 on the other side of the clamping groove 28 to receive a clamp bolt 34. The first clamp bulkhead 30 includes a bolt hole 36 large enough to allow the threaded shaft 38 of the clamp bolt 34 to pass, but small enough to prevent passage of the bolt head 40. The second clamp bulkhead 32 has a threaded bolt hole 42 to receive the threaded shaft 38 of the clamp bolt 34 by screwing the clamp bolt 34 into the threaded bolt hole 42. The clamping groove 28 allows the receiving end 26 of the fixed tube 18 to compress. Together, the clamping groove 28, first clamp bulkhead 30, second clamp bulkhead 32 and clamp bolt 34 form a clamp to secure the adjustable tube 20 within the fixed tube 18 by forcing the fixed tube 18 against and around the adjustable tube 20 to act as an anti-rotation device. The anti-rotation device prevents rotation between the fixed tube 18 and the adjustable tube 20.

The adjustable tube 20 includes an adjustable tube attachment head 44 that attaches to the prosthetic foot 16. Both the prosthetic calf 12 and prosthetic foot 16 are shown in FIG. 2 having a standard attachment end 46. The standard attachment end 46 includes a rounded base 48 with a set screw post 50 extending outward, as shown on the prosthetic foot 16 of FIG. 2. The set screw post 50 includes four set screw surfaces 52 which reduce in size from top 54 to bottom 56 of the set screw post 50, whereby the set screw surfaces 52 slope inward toward the center from top 54 to bottom 56. The fixed tube attachment head 22 and adjustable tube attachment head 44 each include a post hole 58 to receive the set screw post 50. The fixed tube attachment head 22 and adjustable tube attachment head 44 each have a concave rounded surface 60 at the entrance of the post hole 58 to mate against the rounded base 48 of the standard attachment end 46. The fixed tube attachment head 22 and adjustable tube attachment head 44 each include four threaded set screw holes 62. The threaded set screw holes 62 allow set screws 64 to be threaded into the threaded set screw holes 62 and against the set screw surfaces 52 of the set screw post 50, when the set screw post 50 is within either of the fixed tube attachment head 22 or the adjustable tube attachment head 44. The inward sloping of the set screw surfaces 52 aid in preventing accidental disconnection of the fixed tube attachment head 22 and the adjustable tube attachment head 44. Accidental disconnection is prevented as the set screws 64 encounter an increase in width of the set screw post 50 as the pylon 10 pulls away from the set screw post 50. The concave rounded surface 60 of allows for fixed tube attachment head 22 and adjustable tube attachment head 44 to be attached at different angles on the standard attachment end 46, due to the interaction with the rounded base 48.

FIGS. 5-12 show internal components and interaction of the fixed tube 18 and the adjustable tube 20. FIGS. 5-8 show a first embodiment and FIGS. 9-12 show a second embodiment. The differences between the two embodiments create a difference in how adjustments are made to the length of the pylon 10. The pylon 10 of either embodiment is adjusted by first having the clamp bolt 34 unscrewed enough such that the fixed tube 18 is not clamped down on the adjustable tube 20. Unclamping the adjustable tube 20 allows for linear movement of the adjustable tube 20 within the fixed tube 18 and allows rotation between the fixed tube 18 and adjustable tube 20.

Figure 5:
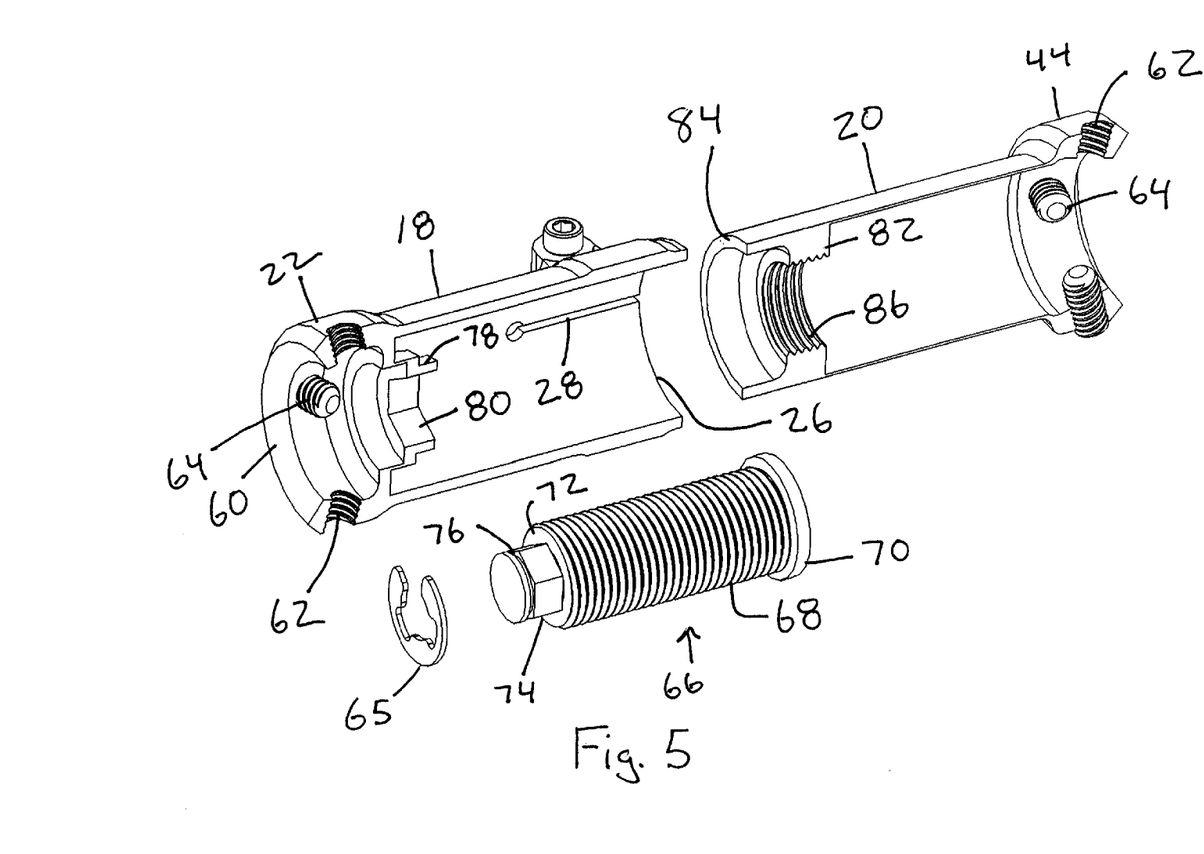
FIG. 5 is a cross sectional view of an adjustable pylon according to the present invention.
Figure 6:
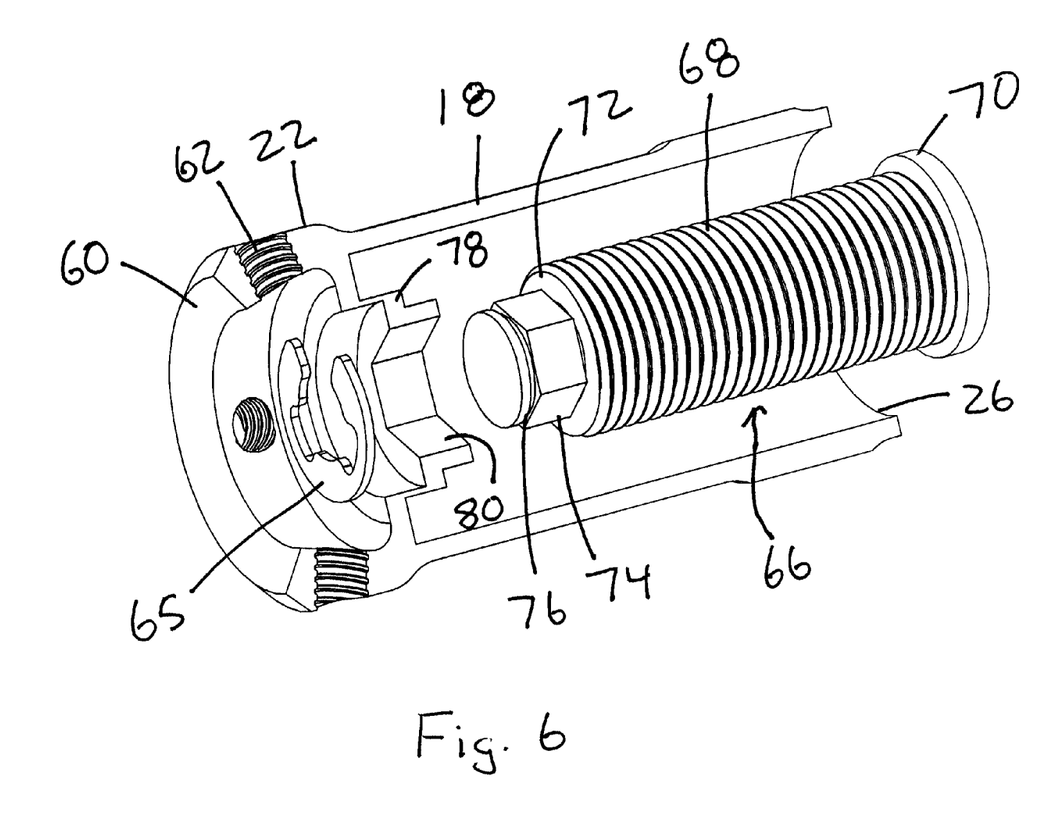
FIG. 6 is a cross sectional view of an adjustable pylon according to the present invention.
Figure 7:
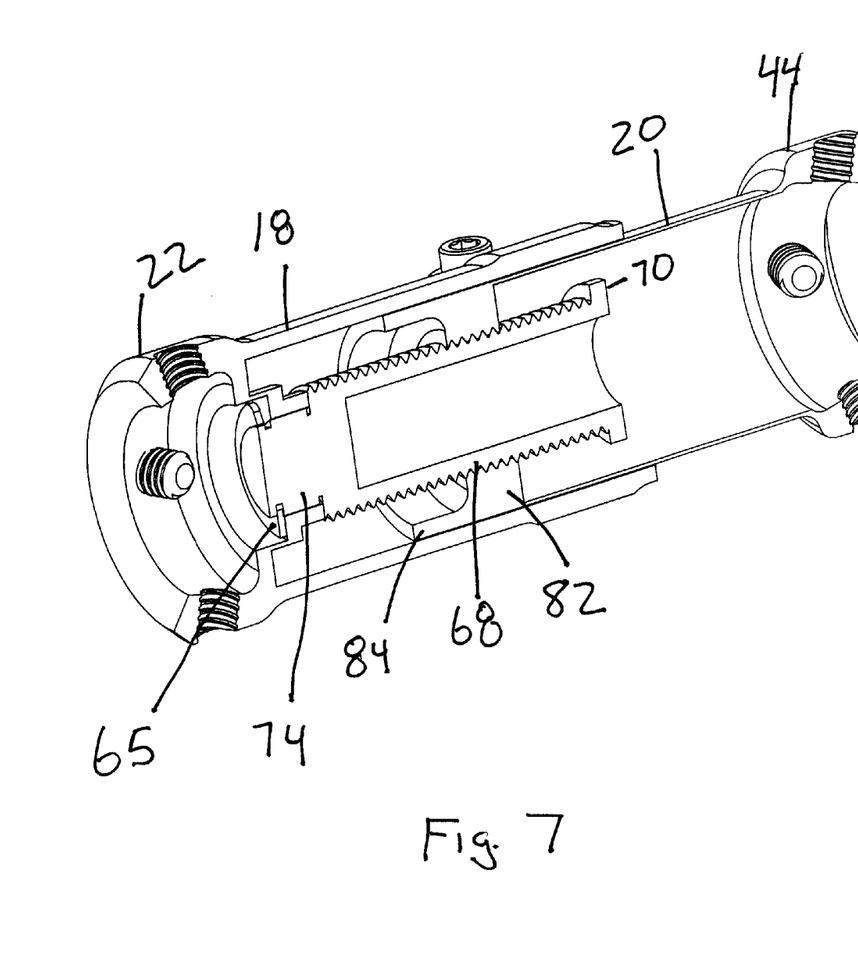
FIG. 7 is a cross sectional view of an adjustable pylon according to the present invention.
Figure 8:
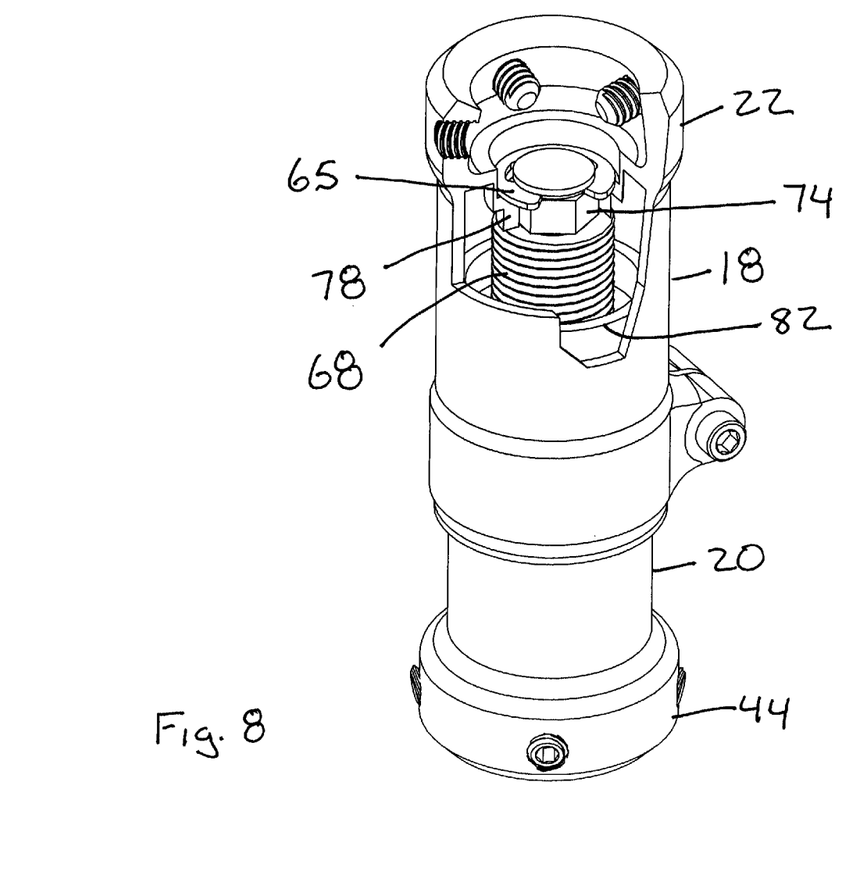
FIG. 8 is a perspective cutaway view of an adjustable pylon according to the present invention.
Figure 9:
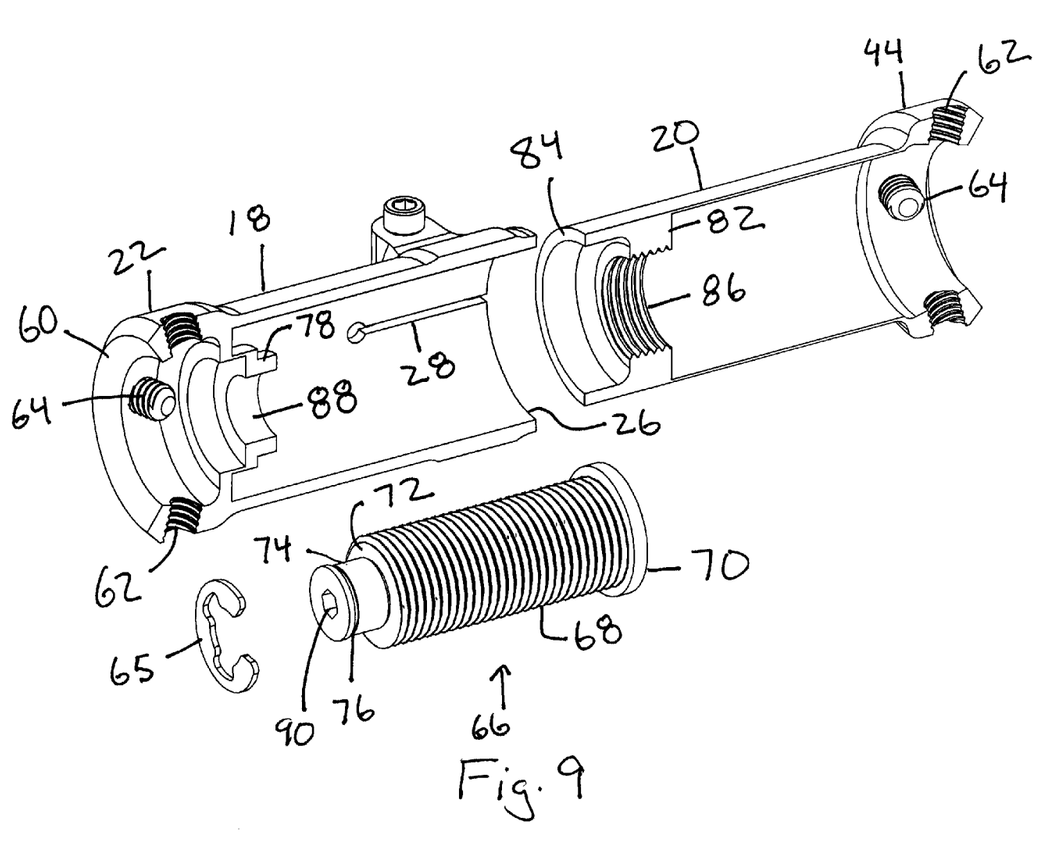
FIG. 9 is a cross sectional view of an adjustable pylon according to the present invention.
Figure 10:
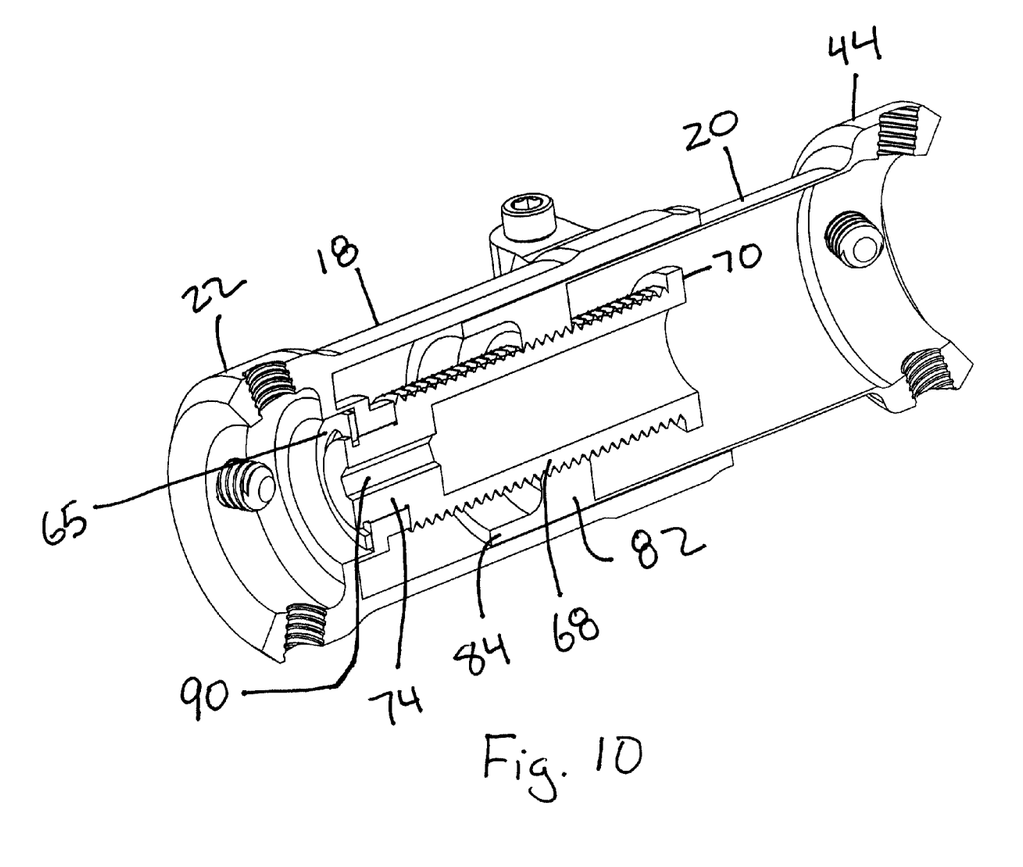
FIG. 10 is a cross sectional view of an adjustable pylon according to the present invention.
Figure 11:
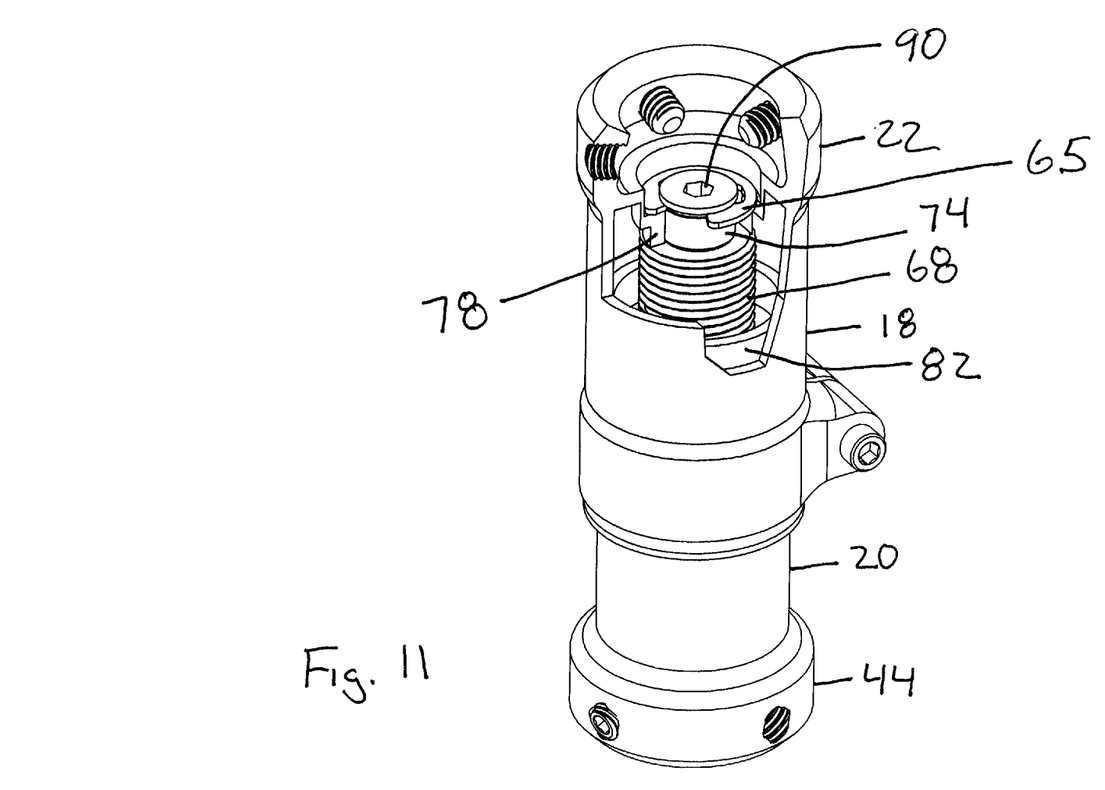
FIG. 11 is a perspective cutaway view of an adjustable pylon according to the present invention.

FIG. 5 shows the fixed tube 18, adjustable tube 20, retaining clip 65 and length adjustment screw 66. The length adjustment screw 66 includes a threaded body 68. On one end of the threaded body 68 is a stop base 70. On the other end of the threaded body is a retaining end 72. The retaining end 72 includes a centering post 74 with a retaining clip groove 76. The centering post 74 of the first embodiment is hex shaped. FIGS. 5-8 show a retainer bulkhead 78 that includes a hex shape hole 80 that matches with the hex shape centering post 74. When the hex shape centering post 74 is placed into the hex shape hole 80, the length adjustment screw 66 cannot rotate about the fixed tube 18. The retaining clip 65 is inserted about the retaining clip groove 76 to prevent removal of the length adjustment screw 66 from the fixed tube 18. FIG. 5 shows a threaded bulkhead 82 near an insert end 84 of the adjustment tube 20, which has a threaded hole 86. The insert end 84 is the first part of the adjustment tube 20 that enters the receiving end 26 of the fixed tube 18. Before the length adjustment screw 66 is inserted into the fixed tube 18, the length adjustment screw 66 is inserted into the adjustable tube attachment head 44 and threaded into the threaded hole 86 of the threaded bulkhead 82 of the adjustable tube 20. The stop base 70 of the length adjustment screw 66 acts as a stop to prevent the length adjustment screw 66 from passing completely through the threaded bulkhead 82 of the adjustable tube 20. The second embodiment differs from the first embodiment at the centering post 74 and the hole 88 in the retainer bulkhead 78. FIGS. 9-12 show a round shaped centering post 74 that fits into round shape hole 88 of the retainer bulkhead 78. The round shape of the centering post 74 and hole 88 allow the length adjustment screw 66 to rotate about the fixed tube 18. The centering post 74 also includes a hex shape hole 90 shown in FIGS. 9-11 to receive a hex shape wrench 92 shown in FIG. 12.

To adjust the length of the pylon 10 in the first embodiment, the user rotates the fixed tube 18 about the adjustable tube 20 or rotates the adjustable tube 20 within the fixed tube 18. Rotating the fixed tube while holding the adjustment tube 20 causes the length adjustment screw 66 to rotate. Rotation of the length adjustment screw 66 within the threaded bulkhead 82 of the adjustable tube 20 causes movement of the adjustable tube 20 in or out of the fixed tube 18. Rotating the adjustment tube 20, while holding the fixed tube 18, causes the adjustment tube 20 to move up or down the length adjustment screw 66. When the proper length adjustment of the pylon 10 is achieved, the clamp bolt 34 is threaded into the second bulkhead 32 to clamp the adjustable tube 20 down and prevent rotation between the fixed tube 18 and the adjustable tube 20. The advantage of the first embodiment is that the length of the pylon 10 can be changed without removing the pylon 10 from either the calf prosthetic 12 or the foot prosthetic 16. The disadvantage is that you can only adjust the length by one full turn about the length adjustment screw 66, if the calf prosthetic 12 and the foot prosthetic 16 are not removed. If the calf prosthetic 12 or the foot prosthetic 16 is removed, adjustments to pylon length can be made by quarter turns about the length adjustment screw 66.

Figure 12:
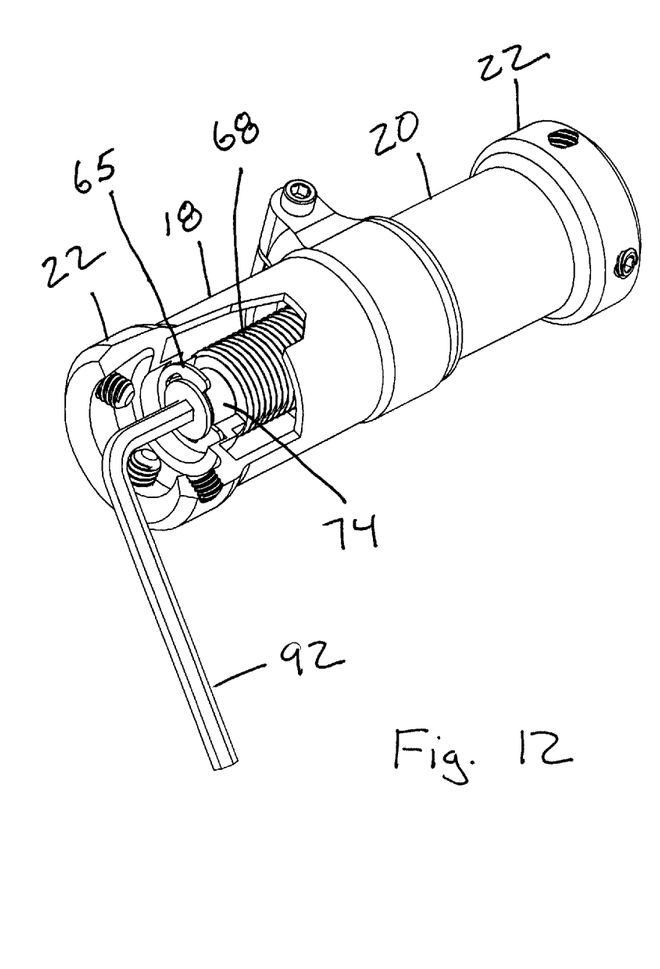
FIG. 12 is a perspective cutaway view of an adjustable pylon according to the present invention.

To adjust the length of the pylon 10 of the second embodiment, the user must remove the pylon 10 from the calf prosthetic 12 to access the hex shape hole 90 using the hex shape wrench 92, as shown in FIG. 12. The hex shape wrench 92 and hex shape hole 90 are used together as a turning device to rotate the length adjustment screw 66. Rotation of the length adjustment screw 66 within the threaded bulkhead 82 of the adjustable tube 20 while holding the adjustable tube 20 causes movement of the adjustable tube 20 in or out of the fixed tube 18. When the proper length adjustment of the pylon 10 is achieved, the clamp bolt 34 is threaded into the second bulkhead 32 to clamp the adjustable tube 20 down and prevent rotation between the fixed tube 18 and the adjustable tube 20. The advantage of the second embodiment is that the length of the pylon 10 can be changed by slight movement of the length adjustment screw 66 to produce slight changes in length of the pylon 10. The disadvantage of the second embodiment is that the calf prosthetic 12 must be removed to change the length of the pylon 10.

While different embodiments of the invention have been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention that is to be given the full breadth of any and all equivalents thereof.

We claim:

1. An adjustable pylon for use with a prosthetic limb, comprising:
    a fixed tube, said fixed tube having an attachment end and a receiving end, said attachment end adapted to attach to a component of the prosthetic limb, said fixed tube including a retainer bulkhead inside said fixed tube, said retainer bulkhead including a hole;
    an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and
    a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;
    further including an anti-rotation device as part of said adjustable pylon to prevent rotation of said adjustable tube within said fixed tube when required; and
    wherein said anti-rotation device includes a clamping groove along said fixed tube at said receiving end of said fix tube, a first clamp bulkhead on said fixed tube at one side of said clamping groove and a second clamp bulkhead on said fixed tube at another side of said clamping groove, and a clamp bolt; said first clamp bulkhead including a bolt hole large enough to allow a threaded shaft of said clamp bolt to pass; and said second clamp bulkhead having a threaded bolt hole.

2. The adjustable pylon of claim 1, wherein said centering post is round and said hole of said retainer bulkhead inside said fixed tube is round such that said length adjustment screw rotates about said hole of said retainer bulkhead inside said fixed tube and wherein said length adjustment screw includes a turning device to allow said length adjustment screw to be rotated within said pylon.

3. The adjustable pylon of claim 1, wherein said centering post and said hole of said retainer bulkhead inside said fixed tube are shaped to interlock such that said length adjustment screw cannot rotate about said hole of said retainer bulkhead inside said fixed tube.

4. An adjustable pylon for use with a prosthetic limb, comprising:
   a fixed tube, said fixed tube having an attachment end and a receiving end, said attachment end adapted to attach to a component of the prosthetic limb, said fixed tube including a retainer bulkhead inside said fixed tube, said retainer bulkhead including a hole;
   an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and
   a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;
   wherein said centering post is round and said hole of said retainer bulkhead inside said fixed tube is round such that said length adjustment screw rotates about said hole of said retainer bulkhead inside said fixed tube and wherein said length adjustment screw includes a tool hole shaped to receive a hand tool to allow said length adjustment screw to be rotated within said pylon using said hand tool.

5. An adjustable pylon for use with a prosthetic limb, comprising:
   a fixed tube, said fixed tube having an attachment end and a receiving end, said attachment end adapted to attach to a component of the prosthetic limb, said fixed tube including a retainer bulkhead inside said fixed tube, said retainer bulkhead including a hole;
   an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and
   a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;
   wherein said centering post and said hole of said retainer bulkhead inside said fixed tube are shaped to interlock such that said length adjustment screw cannot rotate about said hole of said retainer bulkhead inside said fixed tube.

6. An adjustable pylon for use with a prosthetic limb, comprising:
   a fixed tube, said fixed tube having an attachment end and a receiving end, said attachment end adapted to attach to a component of the prosthetic limb, said fixed tube including a retainer bulkhead inside said fixed tube, said retainer bulkhead including a hole;
   an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and
   a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;
   wherein said attachment end of said adjustable tube includes a hole, a concave rounded surface at the entrance said hole of said attachment end of said adjustable tube and at least one set screw hole which leads to said hole of said attachment end of said adjustable tube.

7. An adjustable pylon for use with a prosthetic limb, comprising:
   a fixed tube, said fixed tube having an attachment end and a receiving end, said attachment end adapted to attach to a component of the prosthetic limb, said fixed tube including a retainer bulkhead inside said fixed tube, said retainer bulkhead including a hole;
   an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and
   a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;
   wherein said attachment end of said fixed tube includes a hole, a concave rounded surface at the entrance said hole of said attachment end of said fixed tube and at least one set screw hole which leads to said hole of said attachment end of said fixed tube.

8. An adjustable pylon for use with a prosthetic limb, comprising:
   a fixed tube, said fixed tube having an attachment end and a receiving end, said attachment end adapted to attach to a component of the prosthetic limb, said fixed tube including a retainer bulkhead inside said fixed tube, said retainer bulkhead including a hole;

an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;

further including a retainer device connected to said centering post to retain said centering post in said hole of said retainer bulkhead of said fixed tube in order to retain said adjustable tube inside said fixed tube; and wherein said centering post and said hole of said retainer bulkhead inside said fixed tube are shaped to interlock such that said length adjustment screw cannot rotate about said hole of said retainer bulkhead inside said fixed tube.

9. An adjustable pylon for use with a prosthetic limb, comprising:

a fixed tube, said fixed tube having an attachment end and a receiving end, said attachment end adapted to attach to a component of the prosthetic limb, said fixed tube including a retainer bulkhead inside said fixed tube, said retainer bulkhead including a hole;

an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;

wherein said retainer device includes a retaining clip groove about said centering post and a retaining clip; and wherein said centering post and said hole of said retainer bulkhead inside said fixed tube are shaped to interlock such that said length adjustment screw cannot rotate about said hole of said retainer bulkhead inside said fixed tube.

10. An adjustable pylon for use with a prosthetic limb, comprising:

a fixed tube, said fixed tube having an attachment end and a receiving end, said attachment end adapted to attach to a component of the prosthetic limb, said fixed tube including a retainer bulkhead inside said fixed tube, said retainer bulkhead including a hole;

an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;

further including an anti-rotation device as part of said adjustable pylon to prevent rotation of said adjustable tube within said fixed tube when required; and wherein said centering post and said hole of said retainer bulkhead inside said fixed tube are shaped to interlock such that said length adjustment screw cannot rotate about said hole of said retainer bulkhead inside said fixed tube.

11. An adjustable pylon for use with a prosthetic limb, comprising:

a fixed tube, said fixed tube having an attachment end and a receiving end, said attachment end adapted to attach to a component of the prosthetic limb, said fixed tube including a retainer bulkhead inside said fixed tube, said retainer bulkhead including a hole;

an adjustable tube, said adjustable tubing having an attachment end and an insert end, said attachment end adapted to attach to a component of the prosthetic limb, said insert end sized to fit inside said fixed tube at said receiving end of said fixed tube, said adjustable tube including a threaded bulkhead inside said adjustable tube, said threaded bulkhead including a threaded hole; and a length adjustment screw, said length adjustment screw including a threaded body and a centering post, said threaded body threaded to screw into said threaded hole of said threaded bulkhead inside said adjustable tube where said centering post is inserted first such that said centering post extends towards said hole of said retainer bulkhead of said fixed tube, said centering post sized to insert into said hole of said retainer bulkhead of said fixed tube;

further including a retainer device connected to said centering post to retain said centering post in said hole of said retainer bulkhead of said fixed tube in order to retain said adjustable tube inside said fixed tube;

further including an anti-rotation device as part of said adjustable pylon to prevent rotation of said adjustable tube within said fixed tube when required; and wherein said anti-rotation device includes a clamping groove along said fixed tube at said receiving end of said fix tube, a first clamp bulkhead on said fixed tube at one side of said clamping groove and a second clamp bulkhead on said fixed tube at another side of said clamping groove, and a clamp bolt; said first clamp bulkhead including a bolt hole large enough to allow a threaded shaft of said clamp bolt to pass; and said second clamp bulkhead having a threaded bolt hole.

* * * * *